(12) United States Patent
Schroeder

(10) Patent No.: US 9,884,803 B2
(45) Date of Patent: Feb. 6, 2018

(54) PREPARATION OF HOMOALLYLIC COMPOUNDS BY REACTION OF CYCLOPROPYLVINYL PRECURSORS WITH BRONSTEDT ACIDS

(71) Applicants: Givaudan, S.A., Vernier (CH); Amyris, Inc., Emeryville, CA (US)

(72) Inventor: Fridtjof Schroeder, Hettlingen (CH)

(73) Assignees: Givaudan SA, Vernier (CH); Amyris, Inc., Emeryville, CA (US)

( * ) Notice: Subject to any disclaimer, the term of this patent is extended or adjusted under 35 U.S.C. 154(b) by 0 days.

(21) Appl. No.: 15/031,132

(22) PCT Filed: Oct. 24, 2014

(86) PCT No.: PCT/EP2014/072891
§ 371 (c)(1),
(2) Date: Apr. 21, 2016

(87) PCT Pub. No.: WO2015/059293
PCT Pub. Date: Apr. 30, 2015

(65) Prior Publication Data
US 2016/0251298 A1 Sep. 1, 2016

(30) Foreign Application Priority Data
Oct. 25, 2013 (GB) .................................. 1318894.1

(51) Int. Cl.
| | | |
|---|---|---|
| C07C 67/00 | (2006.01) | |
| C07C 253/30 | (2006.01) | |
| C07C 17/08 | (2006.01) | |
| C07C 29/09 | (2006.01) | |
| C07C 29/124 | (2006.01) | |
| C07C 29/00 | (2006.01) | |
| C07C 29/147 | (2006.01) | |
| C07C 17/04 | (2006.01) | |
| C12P 17/04 | (2006.01) | |

(52) U.S. Cl.
CPC .............. *C07C 67/00* (2013.01); *C07C 17/08* (2013.01); *C07C 29/00* (2013.01); *C07C 29/095* (2013.01); *C07C 29/124* (2013.01); *C07C 29/147* (2013.01); *C07C 253/30* (2013.01); *C12P 17/04* (2013.01); *C07B 2200/09* (2013.01)

(58) Field of Classification Search
CPC ....... C07C 17/08; C07C 253/30; C07C 29/00; C07C 29/095; C07C 29/124; C07C 29/147; C07C 67/00; C12P 17/04
See application file for complete search history.

(56) References Cited

U.S. PATENT DOCUMENTS

| | | | |
|---|---|---|---|
| 5,854,405 A | 12/1998 | Archibald et al. | |
| 2012/0135477 A1 | 5/2012 | Breuer et al. | |
| 2013/0273619 A1* | 10/2013 | Bonnekessel | C07C 29/58 435/126 |

OTHER PUBLICATIONS

Ohtake et al., "5a-Carba-β-D-glucopyranose derivatives as novel sodium-dependent glucose cotransporter 2 (SGLT2) inhibitors for the treatment of type 2 diabetes" *Bioorganic & Medicinal Chemistry*, Elsevier Ltd., Aug. 8, 2011.
Ornstein et al., "2-Substituted (2 SR)-2-Amino-2-((1 SR, 2 SR)-2-carboxycycloprop-1-yl)glycines as Potent and Selective Antagonists of Group II Metabotropic Glutamate Receptors. 2. Effects of Aromatic Substitution, Pharmacological Characterization, and Bioavailability" *Journal of Medicinal Chemistry*, vol. 41, No. 3, Jan. 14, 1998.
Great Britain Search Report in application GB 1318894.1, dated Apr. 28, 2014.
Morandi et al., "Iron-Catalyzed Cyclopropanation in 6 M KOH with in Situ Generation of Diazamethane" *Science*, vol. 335, American Association for the Advancement of Science, Mar. 23, 2012.
Jones et al., "The Cyclopropylidene: Generation and Reactions" *Journal of the American Chemical Society*, vol. 85, No. 18, pp. 2754-2759, Sep. 1, 1963.
Yovell at al., "AlCl3-Induced Reactions of Vinylcyclopropanes" *Tetrahedron*, vol. 34, No. 7, pp. 993-996, Elsevier, 1978.
Mochalov et al., "New Pathway to the Synthesis of Substituted 4H-3,1 Benzoxazines" *Chemistry of Heterocyclic Compounds*, vol. 39, No. 3, Jun. 2003.
Hahn et al., "Electrical Effects of Cycloalkyl Groups" *Journal of the American Chemical Society*, Jun. 19, 1968.
Murahashi et al., "Quintet Carbenes" *Tetrahedron.*, vol. 28, pp. 1485-1496, Pergamon Press 1972.
Cleary et al., "Photochemical Behavior of Cyclopropyl-Substituted Benzophenones and Valerophenones" *Journal of Organic Chemistry*, Mar. 3, 2011.
Varga et al., "Chemical and Biological Investigation of Cyclopropyl Containing Diaryl-pyrazole-3-carboxamides as Novel and Potent Cannabinoid Type 1 Receptor Antagonists" *Journal of Meidinal Chemistry*, vol. 52, No. 9, Jun. 15, 2009.

(Continued)

*Primary Examiner* — Pancham Bakshi
*Assistant Examiner* — Mark R Luderer
(74) *Attorney, Agent, or Firm* — Curatolo Sidoti Co., LPA; Joseph G. Curatolo; Salvatore A. Sidoti

(57) ABSTRACT

A method of forming homoallylic compounds 2 from cyclopropylvinyl precursors 1 in the presence of a Bronsted acid HQ

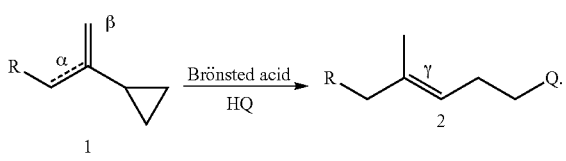

10 Claims, No Drawings

(56) References Cited

OTHER PUBLICATIONS

Gagnon et al., "Palladium-Catalyzed Cross-Copupling Reaction of Tricyclopropylbismuth with Aryl Halides and Triflates" *Journal of Organic Chemistry*, vol. 73, No. 9, Mar. 26, 2008.

Matsuda et al., "Activation of a Cyclobutanone Carbon-Carbon Bond over an Aldehyde Carbon-Hydrogen Bond in the Rhodium-catalyzed Decarbonylation" *Chemistry Letters*, vol. 35, No. 3, Feb. 11, 2006.

Fráter et al., "Synthesis and Olfactory Properties of (−)-(1R,2S)-Georgywood" *Tetrahedron: Assymetry*, Elsevier Science Publishing, Nov. 3, 2004.

Khusnutdinov et al. "Hydrochlorination of Unsaturated Compounds by the Action of $CH_2Cl_2$ or $CHCl_3$ and Rhodium Complexes" *Bulletin of the Academy of Science of the USSR*, vol. 40, Issue 6, pp. 1213-1217, Jun. 1991.

International Search Report and Written Opinion in PCT/EP2014/072891, dated Feb. 13, 2015.

Pellissier, "Recent Developments in the reactivity of methylene- and alkylidenecyclopropane derivatives" *Tetrahedron*, Elsevier Science Publishing, Aug. 26, 2010, Amsterdam, NL.

Wen-Jian Shi, et al, "Gold(I)- and Brønsted Acid-Catalyzed Ring-Opening of Unactivated Vinylcyclopropanes with Sulfonamides", Advanced Synthesis & Catalysis, vol. 349, No. 10, Jul. 2, 2007, pp. 1619-1623, Wiley-VCH Verlage GmbH & Co.

\* cited by examiner

PREPARATION OF HOMOALLYLIC COMPOUNDS BY REACTION OF CYCLOPROPYLVINYL PRECURSORS WITH BRONSTEDT ACIDS

CROSS REFERENCE TO RELATED APPLICATIONS

This application is a national stage application of International Application No. PCT/EP2014/072891, filed 24 Oct. 2014, which claims priority from Great Britain Patent Application No. 1318894.1, filed 25 Oct. 2013, which applications are incorporated herein by reference.

The present invention is concerned with a process of preparing homoallylic compounds from cyclopropylvinyl precursors. The invention is also concerned with the use of the homoallylic compounds as useful intermediates in the preparation of flavor and fragrance ingredients.

The rearrangement reaction of 1-substituted cyclopropylvinyl precursors β-1 to compounds of the structure 2 using various reaction conditions and reagents has been reported in the literature

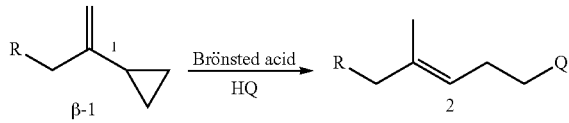

and substituted benzenesulfonamides under Au(I)- or triflic acid-catalysis (A. Togni et al., *Adv. Synth. & Cat.* 349, 1619 (2007); triethylsilane or triethoxysilane and Wilkinson's catalyst (I. P. Beletskaya et al., *Tetrahedron Lett.* 3, 7901, 1995); ethyl propiolate and diphenyl diselenide (A. Ogawa et al., *J. Org. Chem.* 65, 7682, 2000); Wilkinson's catalyst in dichloromethane or chloroform (R. I. Khusnutdinov et al., *Izvestiya Akademii Nauk SSSR, Seriya Khimicheskaya*, 1373, 1991) and trimethylsilyl halides (W-D. Z. Li, J.-H. Yang, *Org. Lett.* 6, 1849, 2004) have been used for this transformation.

In all these examples, however, relatively expensive and/or hazardous reactants are used, which are problematic for use on an industrial scale. Furthermore, relatively high amounts (10%) of expensive catalysts such as Au(I), Ag(I), triflic acid, Rh(I) or stoichiometric amounts of additives such as diphenyl diselenide are necessary.

Accordingly, the invention provides in a first aspect a method of forming homoallylic compounds 2 from cyclopropylvinyl precursors 1 in the presence of a Bronsted acid HQ

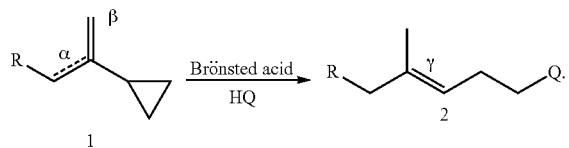

wherein, the Bronsted acid HQ is selected from $R'CO_2H$ and/or a hydrogen halide selected from HCl, HBr or HI, wherein R is a $C_{1-30}$ cyclic, polycyclic or acyclic alkyl residue, or an aryl or polyaryl residue, each of which may be saturated or unsaturated, branched or linear, and substituted or unsubstituted; R' is a $C_{1-30}$ alkyl or aryl residue, which may be linear or branched and may be substituted or unsubstituted, and wherein Q is an ester group and/or a halide atom.

The compound 2 may be hydrolysed under conditions known from the literature to a homoallylic alcohol 3

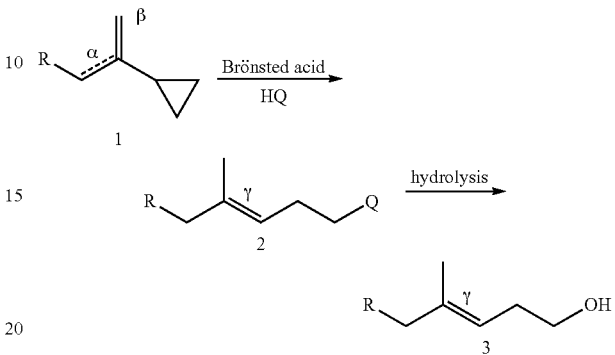

When hydrogen halides (HQ=HX) are added to vinylcyclopropane 1 the rearrangement products are homoallylic halides 2' (with Q=X=Cl, Br, I) which can be easily converted through nucleophilic substitution with potassium carboxylates $R'CO_2^-K^+$ to esters of the general structure 2 (Q=$R'CO_2$) in the presence of a phase transfer catalyst (PTC), as described for example for X=Br in the literature (Nefedov et al., *Org. Prep. Proc. Int.* 22, 215, 1990). The resulting esters of the general structure 2 (Q=$R'CO_2$) can be hydrolyzed with aqueous base to homoallylic alcohols of the general structure 3. The whole sequence (from 2' to 3) proceeds without erosion of the E/Z-ratio, so that the E/Z-ratio of 3 is the same one as in 2' under the usual reaction conditions.

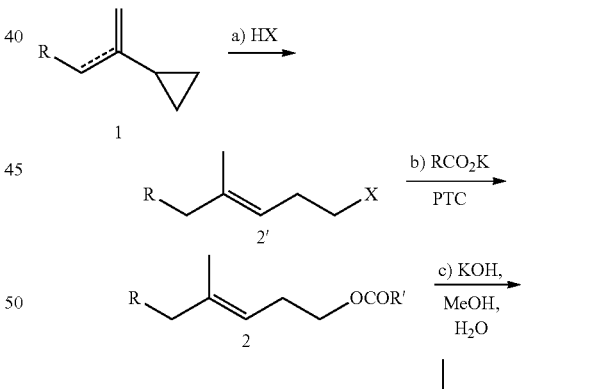

The resulting 4,4-disubstituted homoallylic alcohols 3 and the esters 2 (Q=$R'CO_2$) have interesting sensory properties and/or can serve as precursors for other flavor and fragrance ingredients.

Particularly surprising was the finding that the rearrangement reaction of the present invention proceeded without the need for transition metal catalysis, or any other reagent or solvent (in particular, additional non-polar organic solvents such as dichloromethane) other than water and/or alkanoic acid HQ.

As organic acids there may be employed HQ of the type R'CO$_2$H, bis-acids such as malonic acid, triacids such as citric acid and aminoacids. However, for reasons of cost efficiency it is preferred to use low molecular weight and inexpensive acids such as formic acid, acetic acid, propionic acid and chloroacetic acid.

Some of the reactants HQ have been used for the cyclopropylcarbinyl rearrangement of tetrasubstituted vinylcyclopropanes, for example hydrogen halides (Y. Nagamoto, Y. Takemoto, K. Takasu et al, *Synlett* 24, 120, 2013) or trifluoroacetic acid (A. G. Griesbeck et al., *J. Org. Chem.* 60, 1952, 1995). It was nevertheless surprising that the HX addition to β-1 with rearrangement of monosubstituted cyclopropylvinyl precursors β-1 to 2 could proceed cleanly, because it is known that the exo-methylene group in β-1 is more sensitive to side reactions, such as oligomerization and polymerization, than cyclopropane alkenes with 1,2-disubstituted double bonds or a higher degree of substitution grade on the alkene functionality. Furthermore, Bronsted acid addition and cyclopropylcarbinyl rearrangement of 1,2-disubstituted vinylcyclopropane α-1, to 2 was completely unknown so far to the best knowledge of the applicant.

The prior art teaches the skilled person that the outcome of cyclopropylcarbinyl rearrangement reactions is usually affected by the substitution pattern on the alkene moiety which is due, in part, to the stereoelectronic properties of the intermediate cyclopropylcarbinyl cation (G. A. Olah et al., *Chem. Rev.* 92, 69-95, 1992). This means that reaction conditions that give a desired cyclopropylcarbinyl rearrangement product, would not necessarily provide a similar result on differently substituted substrates.

The rearrangement reaction of the present invention starting from vinylcyclopropane substituted substrates 1, gives rearranged 4,4-disubstituted homoallylic halides and esters 2 with relatively high E/Z-selectivities. These selectivities are usually around 75:25, but generally higher than 70:30, and preferentially higher than 80:20.

The cyclopropyl alkene substrates employed according to the invention can exist in the form of the β-isomer (β-1) or the α-isomer (α-1). In the presence of the Bronsted acid HQ the isomers might equilibrate before rearranging to 2. Therefore, in accordance with the present invention, one can use the α- or the β-isomer or mixtures of both as substrates.

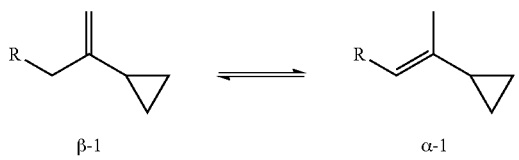

In a specific embodiment of the present invention, the radical R on the contains unsaturation and may be linear or branched, acyclic, cyclic and polycyclic. In an even more specific embodiment of the present invention, the vinyl cyclopropane substrate 1 may be structurally derived from polyprenoids such as myrcene, farnesene and higher polyprenoids.

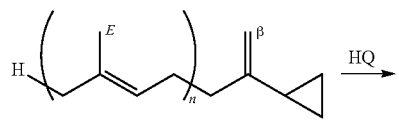

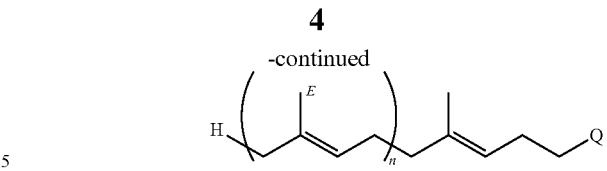

in which n=1, 2 or 3.

It was particularly surprising that under the acidic conditions of the Bronsted acid addition to a vinyl cyclopropane substrate 1 containing additional unsaturation such as in the case of the polyprenoids, only the alkene group of the vinyl cyclopropane underwent a carbocationic reaction and that the trisubstituted distal double bonds did not participate in the rearrangement.

This surprising finding was in strong contrast to the teaching in the prior art that polyprenes usually cyclize with strong Bronsted acids in a completely different way, that is, one of the distal tri-substituted double bonds, preferentially the terminal (western) one, is protonated first and the next double bond cyclizes into the arising carbocation.

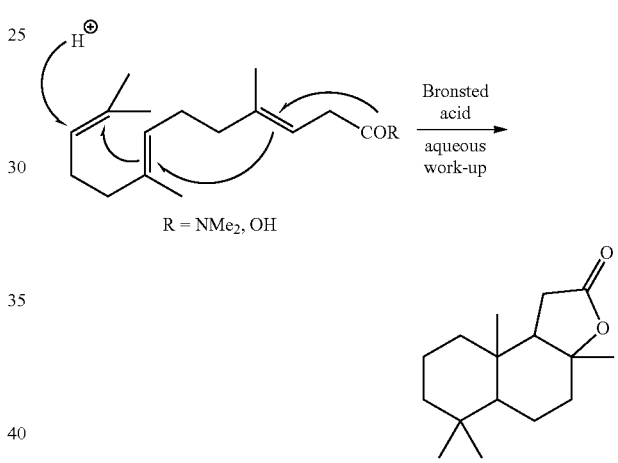

This cyclisation, known from the literature, proceeds in the presence of stoichiometric amounts of Bronsted acids such as sulfuric acid in formic acid at 40° C. (G. Lucius, *Chem. Ber.* 93, 2663, 1960), methanesulfonic acid in dichloromethane at −15° C. (DE 4301555, Henkel KGaA, 1993)

or sulfuric acid in toluene at 0° C. (EP 2048139, Kao Corporation, 2006)

In the light of this prior art teaching it was entirely surprising that in vinyl cyclopropane substrates 1 containing additional unsaturation such as in the case of the polyprenoids, the tri-substituted double bonds remain inert in the presence of Bronsted acids in accordance with the conditions of the present invention. Based on the prior art teaching, the skilled person would not have considered it possible to prepare the homoallylic compounds 2 and 3 of the present invention.

In accordance with a particular aspect of the present invention, depending on the E/Z- and α,β-purity of the polyprene substrate 1, different double bond isomers or isomer mixtures can be used as starting materials to give after cyclopropylcarbinyl rearrangement, the compounds 2.

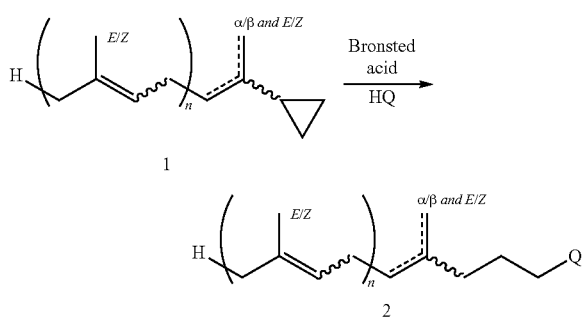

Examples of polyprene type compounds that may be produced in a method according to the present invention is homofarnesyl acetate 2a as well as homofarnesol 3a. Homofarnesol 3a, is a particularly interesting intermediate because especially the correct E,E-configuration of 3a provides, after cyclization under conditions known in the art, the very valuable fragrance ingredient known as Ambrox with a high content of the desired olfactorily active 3aR,5aS,9aS,9bR-isomer.

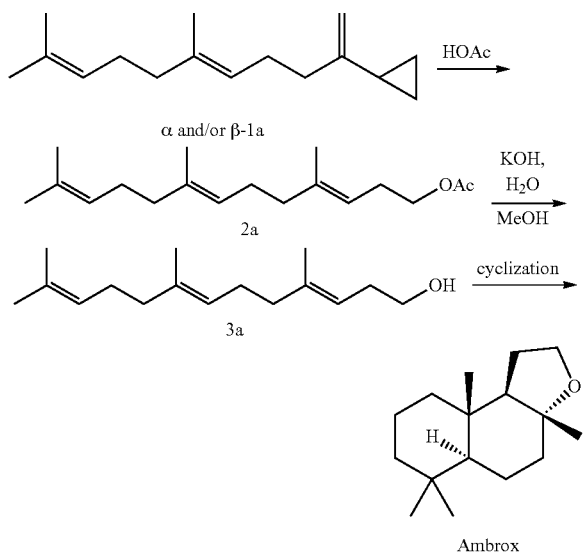

Accordingly, in another aspect of the present invention, there is provided a method of preparing Ambrox, comprising the step of cyclizing E,E-homofarnesol 3a using bacterial enzyme, such as squalene hopene cyclase, said E,E-homofarnesol 3a being prepared from the cyclopropanated beta-farnesene β-1a using a Bronsted acid according to a process defined herein.

The cyclopropanated beta-farnesene β-1a may be prepared from the sesquiterpene beta-farnesene (7,11-dimethyl-3-methylene-1,6,10-dodecatriene). An example of a commercial form of beta-farnesene is obtainable under the trade name BIOFENE™, from Amyris.

Beta-Farnesene, is found in various biological sources including, but not limited to aphids and essential oils, such as peppermint oil. In some plants such as wild potato, beta-farnesene is synthesized as a natural insect repellent. Biochemically, beta-farnesene can be made from FPP by beta-farnesene synthase. Some non-limiting examples of suitable nucleotide sequences that encode such an enzyme include (AF024615; *Mentha*piperita*) and (AY835398; *Artemisia annua*). See Picaud et al., Phytochemistry 66(9): 961-967 (2005).

Beta-farnesene can be derived from any source or prepared by any method known to a skilled artisan. In some embodiments, beta farnesene is derived from a chemical source (e.g., petroleum or coal) or obtained by a chemical synthetic method. In other embodiments, it is prepared by fractional distillation of petroleum or coal tar. In further embodiments, it is prepared by any known chemical synthetic method. One non-limiting example of suitable chemical synthetic method includes dehydrating nerolidol with phosphoryl chloride in pyridine.

In some embodiments, it can be obtained or derived from naturally occurring terpenes that can be produced by a wide variety of plants, such as *Copaifera langsdorfii*, conifers, and spurges; insects, such as swallowtail butterflies, leaf beetles, termites, and pine sawflies; and marine organisms, such as algae, sponges, corals, mollusks, and fish.

*Copaifera langsdorfii* or *Copaifera* tree is also known as the diesel tree and kerosene tree. It has many names in local languages, including kupa'y, cabismo, and copaúva. *Copaifera* tree may produce a large amount of terpene hydrocarbons in its wood and leaves. Generally, one *Copaifera* tree can produce from about 30 to about 40 liters of terpene oil per year.

Terpene oils can also be obtained from conifers and spurges. Conifers belong to the plant division Pinophyta or Coniferae and are generally cone-bearing seed plants with vascular tissue. The majority of conifers are trees, but some conifers can be shrubs. Some non-limiting examples of suitable conifers include cedars, cypresses, douglas-firs, firs, junipers, kauris, larches, pines, redwoods, spruces, and yews. Spurges, also known as *Euphorbia*, are a very diverse worldwide genus of plants, belonging to the spurge family (Euphorbiaceae). Consisting of about 2160 species, spurges are one of the largest genera in the plant kingdom.

Beta-farnesene is a sesquiterpene. Sequiterpenes are part of a larger class of compounds called terpenes. A large and varied class of hydrocarbons, terpenes include hemiterpenes, monoterpenes, sesquiterpenes, diterpenes, sesterterpenes, triterpenes, tetraterpenes, and polyterpenes. As a result, beta farnesene can be isolated or derived from terpene oils for use in the present invention.

In certain embodiments, beta farnesene is derived from a biological source. In other embodiments, it can be obtained from a readily available, renewable carbon sources. In further embodiments, it is prepared by contacting a cell capable of making beta farnesene with a carbon source under conditions suitable for making it.

Any carbon source that can be converted into one or more isoprenoid compounds can be used herein. In some embodiments, the carbon source is a sugar or a non-fermentable carbon source. The sugar can be any sugar known to those of skill in the art. In certain embodiments, the sugar is a monosaccharide, disaccharide, polysaccharide or a combination thereof. In other embodiments, the sugar is a simple sugar (a monosaccharide or a disaccharide). Some non-limiting examples of suitable monosaccharides include glucose, galactose, mannose, fructose, ribose and combinations thereof. Some non-limiting examples of suitable disaccharides include sucrose, lactose, maltose, trehalose, cellobiose and combinations thereof. In still other embodiments, the simple sugar is sucrose. In certain embodiments, the bioengineered fuel component can be obtained from a polysaccharide. Some non-limiting examples of suitable polysaccharides include starch, glycogen, cellulose, chitin and combinations thereof.

The sugar suitable for making the beta-farnesene can be found in a wide variety of crops or sources. Some non-limiting examples of suitable crops or sources include sugar cane, bagasse, miscanthus, sugar beet, sorghum, grain sorghum, switchgrass, barley, hemp, kenaf, potatoes, sweet potatoes, cassava, sunflower, fruit, molasses, whey or skim milk, corn, stover, grain, wheat, wood, paper, straw, cotton, many types of cellulose waste, and other biomass. In certain embodiments, the suitable crops or sources include sugar cane, sugar beet and corn. In other embodiments, the sugar source is cane juice or molasses.

A non-fermentable carbon source is a carbon source that cannot be converted by the organism into ethanol. Some non-limiting examples of suitable non-fermentable carbon sources include acetate and glycerol.

In certain embodiments, beta farnesene can be prepared in a facility capable of biological manufacture of C15 isoprenoids. The facility can comprise any structure useful for preparing the C15 isoprenoids, such as beta-farnesene, using a microorganism. In some embodiments, the biological facility comprises one or more of the cells disclosed herein. In other embodiments, the biological facility comprises a cell culture comprising at least a C15 isoprenoid in an amount of at least about 1 wt. %, at least about 5 wt. %, at least about 10 wt. %, at least about 20 wt. %, or at least about 30 wt. %, based on the total weight of the cell culture. In further embodiments, the biological facility comprises a fermentor comprising one or more cells.

Any fermentor that can provide cells or bacteria a stable and optimal environment in which they can grow or reproduce can be used herein. In some embodiments, the fermentor comprises a culture comprising one or more of the cells disclosed herein. In other embodiments, the fermentor comprises a cell culture capable of biologically manufacturing farnesyl pyrophosphate (FPP). In further embodiments, the fermentor comprises a cell culture capable of biologically manufacturing isopentenyl diphosphate (IPP). In certain embodiments, the fermentor comprises a cell culture comprising at least a C15 isoprenoid in an amount of at least about 1 wt. %, at least about 5 wt. %, at least about 10 wt. %, at least about 20 wt. %, or at least about 30 wt. %, based on the total weight of the cell culture.

Biosynthetic approaches to making beta farnesene via various routes are described in U.S. Pat. No. 7,399,323. In particular the production of beta farnesene is described via the MEV pathway in *Escherichia coli* host strains; via the DXP pathway in an *Escherichia coli* host strain; via *Saccharomyces cerevisiae* host strains; and via an *Escherichia coli* host strain in an aerobic, nitrogen-limited, fed-batch cultivation. Other approaches are described in US 2008/0274523; and PCT Publication Numbers WO 2007/140339 and WO 2007/139924.

The vinylcyclopropanated substrates 1, many of which are novel compounds, form another aspect of the present invention.

In a particular embodiment of the present invention there is provided cyclopropanated isoprenes according to the formula

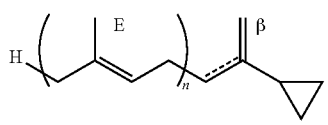

in which n=0, 1, 2 or 3.

Particular compounds include cyclopropanated isoprene, ocimene, myrcene, farnesene. Depending on the E/Z- and α,β-purity of the polyprene different double bond isomers or isomer mixtures can be used as starting material for a cyclopropanation reaction.

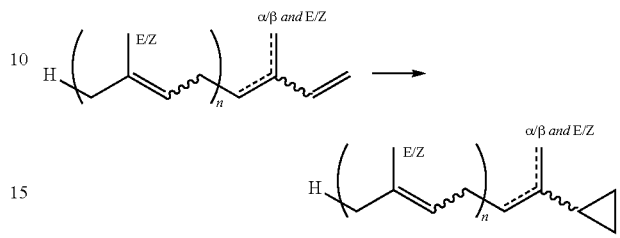

The process of cyclopropanating a double bond to provide the vinylcyclopropanated substrates 1 may proceed using any convenient reagent for carrying out the cyclopropanation of carbon-carbon multiple bonds, such as diazo compounds, in particular diazomethane. Any source of diazomethane may be employed, however, due to the hazards of handling diazomethane, it is preferred to use reagents that will produce diazomethane in-situ. Such reagents include N-methyl-N-nitroso urea (MNU), or the less toxic compound N-methyl-N-nitroso-p-toluenesulfonamide (Diazald®). Cyclopropanation using any of these reagents according to prior art techniques is contemplated in the present invention.

In another aspect of the invention, a novel process of forming the vinylcyclopropanated substrates 1 is provided.

In accordance with another aspect of the present invention there is provided a process of cyclopropanating an alkene substrate, the process comprising the steps of reacting an organic solution of N-alkyl-N-nitroso compound with the substrate, wherein the solution of N-alkyl-N-nitroso compound is generated in-situ or in liquid phase, and without being isolated in pure form, before being added to the substrate.

The N-alkyl-N-nitroso compound might be selected from any compound suitable to generate diazomethane (DAM). Preferably, the N-alkyl-N-nitroso compound is a N-methyl-N-nitroso compound (MNC). In particular, the compound might be selected from the group consisting of N-methyl-N-nitroso-urea (MNU), N-methyl-N-nitroso-p-toluenesulfonamide (Diazald™), N-nitroso-dimethylurethane, nitroso-EMU and N-nitroso-β-methylaminoisobutyl methyl ketone (Liquizald™).

The invention is not limited to any particular N-alkyl-N-nitroso compound; however, further aspects will be explained on the example of N-methyl-N-nitroso-urea (MNU).

MNU may be generated in-situ or in liquid phase from a biphasic system comprising an aqueous phase containing methylurea, $NaNO_2$, an acid; and an organic solvent for receiving the MNU once it is formed. Alternatively, instead of using methylurea, one can generate this in-situ or in liquid phase using methylamine and urea.

Once the MNU is formed, it partitions into the organic solvent provided for that purpose. Once conversion is complete, the organic phase can then be separated from the aqueous phase in a phase separation step, before being added to an alkene substrate, without having to isolate the MNU in solid form. As the MNU is in an organic solvent, it can be cleanly and simply transferred into a reaction vessel containing the alkene substrate.

In a particular embodiment of the present invention there is provided a process of converting a carbon-carbon double bond to a cyclopropane ring, comprising the steps of:
I) reacting an aqueous mixture of urea, methylamine, $NaNO_2$, and an acidic to form MNU,
II) adding an organic solvent for the MNU to form a biphasic mixture, and partitioning the MNU into the organic solvent; and
III) transferring the MNU dissolved in the organic solvent onto a mixture comprising an alkene substrate, aqueous base and catalyst, thereby to cyclopropanate the alkene substrate.

In a particular embodiment of the invention, the organic solvent for MNU is of lower density than the aqueous phase in order that it will float above the aqueous phase and allow the lower aqueous phase to be removed efficiently under gravity in a phase separation step. Ethers are particularly useful organic solvents in this regard.

In order that MNU readily partitions into the organic phase, it is preferred that the organic solvent is rather polar. Suitable solvents therefore, are polar ethers such as tetrahydrofurane (THF), 2-methyl-tetrahydrofurane (MeTHF), dimethoxyethane (DME), dimethylisosorbide (DMIS), or mixtures of these ethers with other co-solvents, which will still allow phase separation to occur between the aqueous phase and the organic phase.

Although ethers are particularly suitable organic solvents, other solvents can be employed. In particular, applicant has found that MNU can partition effectively into amide-type solvents such as N-Methyl-2-pyrrolidone (NMP). However, solutions of MNU in N-alkylpyrrolidones or similar amide solvents are inherently unstable due to the basic properties of these solvents. Indeed, MNU will decompose in basic solvents to diazomethane. If these solvents are to be employed, they are best employed in reactions in which a high stationary inventory of MNU in solvent is not generated. For example, the amide solvents can be particularly effective for use in flow chemistry, wherein only very small amounts of MNU in solvent is formed before it is immediately consumed by reacting with an alkene substrate.

The process described herein carried out under flow conditions in a flow reactor represents a further aspect of this invention.

Whereas, it is known in the art to produce MNU from $NaNO_2$, methylamine, urea and an acid (e.g. in the presence of concentrated sulphuric acid), the reaction is carried out expressly to form MNU as a solid and to isolate it from the liquid phase by filtration. In contradistinction, the means by which MNU is isolated in the present invention present invention is by phase separation into a suitable organic solvent. Phase separation is effected when a suitable organic solvent is added to the aqueous phase. The organic solvent may be introduced either before or after addition of the acid (e.g. sulphuric acid), although addition of the organic solvent before acidification avoids the possibility of any precipitation of solid MNU, which would have to be subsequently dissolved.

Considering that the organic solvent has to be polar in order to promote the partitioning of MNU into the organic phase, it was surprising that a good separation between the organic and aqueous layers could be achieved. Good separation is important if the phase separation step is to be carried out efficiently and with the assurance that significant amounts of MNU are not left in the aqueous phase, which is collected as waste. Accordingly, in a preferred embodiment salts are added to the biphasic mixture before phase separation is undertaken. Inorganic and organic salts or salt mixtures may be added to enhance phase separation and extraction of MNU into the organic phase. Furthermore, water, organic solvents and ionic liquids may be added to avoid undesired precipitation of the reaction components during processing.

MNU is readily obtained from stoichiometric amounts of methylamine hydrochloride, urea, $NaNO_2$ and sulphuric acid, or any other organic or inorganic acid and mixtures of acids. These compounds may be mixed in different ratios but ideally between 1:1:1:<1 and 3:3:1:<1. For the purpose of ease of subsequent phase separation and cyclopropanation the ratio may be more particularly 2:2:1:<1.

In an alternative embodiment, when instead of employing an methylamine hydrochloride and urea, one uses directly methylurea, the ratio of alkyl urea, $NaNO_2$ and sulphuric acid may be between 1:1:<1 and 3:3:<1. For the purpose of ease of subsequent phase separation and cyclopropanation the ratio may be more particularly 2:2:<1.

A variety of transition metal catalysts can be employed in a process according to the present invention, although palladium catalysts are particularly useful. Examples of suitable catalysts are described by Nefedov et al. in Izvestiya Akademii Nauk SSSR, Seriya Khimicheskaya 8, 1861-1869 (1989). Palladium catalysts, e.g. $Pd(acac)_2$, $Pd(OAc)_2$ or $PdCl_2$ are particularly useful when ethylene and mono- or disubstituted alkene substrates are to be cyclopropanated. The mono- or di-substituted alkene substrates may be substituted with any desirable substituents, including but not limited to alkyl or aryl, (both of which may be substituted, branched or strained, and include heteroatoms such as nitrogen, oxygen, sulphur or boron) or a carbonyl group (such as in esters, ketones or aldehydes).

The amount of catalyst employed in a process according to the present invention may be less than 0.5%, less than 0.1 mol %, less than 0.05 mol % and preferably 0.02 mol % or less. Thus in a particular embodiment of this invention Pd-catalysts are used in lower amounts than in the prior art, which describes lowest amounts of 0.06 mol % $Pd(P(OMe)_3)_4$ for the in situ cyclopropanation of a strained alkene (Nefedov, vide supra 1992).

The fact that the applicant was able to carry out highly efficient transition metal catalysed cyclopropanation was surprising. A potential problem of using MNU isolated by phase separation from an aqueous layer containing amines, is that some ammonium and sulfate salts may be carried over into the organic phase and into the reaction vessel containing alkene substrate and transitional metal catalyst. However, whereas it is well known that such impurities can impair the efficiency of transition metal catalyzed reactions, as pointed out by Nefedov (vide supra, 1989) for example, applicant did not encounter any impairment.

FIG. 1 is a schematic representation of a specific embodiment that illustrates the process according to the invention. In a first reaction vessel MNU-precursor I is formed from a mixture of $NaNO_2$, methyl amine and urea in an aqueous medium. An organic solvent is added to this aqueous phase and the whole is pumped onto concentrated acid in a second vessel where after elimination of water, MNU is formed. Alternatively the organic solvent can be added at this stage. Phase separation is carried out in the same vessel (2). The lower aqueous salt solution phase is drained off to waste, whereas the upper organic layer containing the generated MNU is pumped into a third vessel containing the alkene substrate, aqueous basic phase and catalyst. The cyclopropanation reaction proceeds as the two phases are mixed with vigorous stirring, and after the reaction is complete the organic phase containing the cyclopropanated alkene is recovered.

As the acid quench of MNU precursor I in vessel 2 is highly exothermic and the cyclopropanation in vessel 3 is also temperature sensitive, cooling is preferably used for these two steps. In a first aspect, uncontrolled decomposition of MNU needs to be avoided, which might occur above 20° C. and produces methyl isocyanate (MIC). Furthermore, the cyclopropanation is preferably carried out at lower temperature, to avoid release of the low-boiling diazomethane (bp=−23° C.) into the atmosphere and/or dimerization of this reagent to ethylene and nitrogen, which decreases the efficiency of the cyclopropanation step. Both steps are therefore preferably carried out under cooling, e.g. at −20 to +10° C., more preferably around 0° C. These temperatures are nevertheless easily maintained and controlled by the addition rate of MNU precursor I to the acid (step 1) or the addition rate of MNU to the alkene substrate. In flow reactors it should be possible to use higher reaction temperatures.

This set up is relatively non-complex and has the considerable advantage that it avoids separation and handling of solid MNU and reduces human exposure to MNU and diazomethane to a minimum as MNU is generated only in vessel 2 and destroyed (by cyclopropanation) in vessel 3. Furthermore some steps of the reaction sequence can be run in flow reactors, e.g. the MNU generation step (vessel 2), and the phase separation step can be automatized.

Any unreacted diazomethane can be quenched after the reaction is complete, by the addition of a sacrificial alkene with high reactivity (such as ethylene, styrene, limonene, myrcene or farnesene) or alternatively or additionally, acetic acid or other carboxylic acid, which in the presence of a strong base will decompose any diazomethane by methylation of the acid.

The cyclopropanation process has the advantage that any stationary concentration of DAM generated from MNU or any other suitable N-alkyl-N-nitroso compound is kept close to zero. This enhances the safety of the process significantly and prevents the formation of toxic byproducts.

The preparation of homo allylic compounds, such as homo-allylic alcohols via the cyclopropanated compounds, formed using the MNU-mediated chemistry referred to hereinabove represents a very efficient means of obtaining valuable compounds, such as homofarnesol, with high E/Z selectivity. In particular, the methodology described herein represents a very efficient way of producing E,E-homofarnesol. E,E-homofarnesol is a very valuable chemical intermediate for many industries. In particular, E,E-homofarnesol possesses the right number of carbon atoms (16) and the correct E,E-isomeric purity to be easily converted to the very valuable fragrance ingredient known as Ambrox.

There now follows a series of examples that further act to illustrate the invention.

General Analytical Conditions:

Non-polar GCMS: 50° C./2 min, 20° C./min 200° C., 35° C./min 270° C. GC/MS Agilent 5975C MSD with HP 7890A Series GC system. Non-polar column: BPX5 from SGE, 5% phenyl 95% dimethylpolysiloxan 0.22 mm×0.25 mm×12 m. Carrier Gas: Helium. Injector temperature: 230° C. Split 1:50. Flow: 1.0 ml/min. Transfer line: 250° C. MS-quadrupol: 106° C. MS-source: 230° C.

Non-polar GC was used to determine the E/Z-ratios (which were confirmed by NMR-analysis). Non-polar GC: 100° C., 2 min, 15° C. pro min, 240° C., 5 min. Column: DB5 (Agilent) 30 m (1)×0.32 (d) mm×0.25 (thickness) Carrier: Helium (70 kPa). Injector: 240° C. Split: 1:50. Detector (FID): 270° C.

EXAMPLE 1

Preparation of ((5E)-6,10-dimethylundeca-2,5,9-trien-2-yl)cyclopropane α-1a

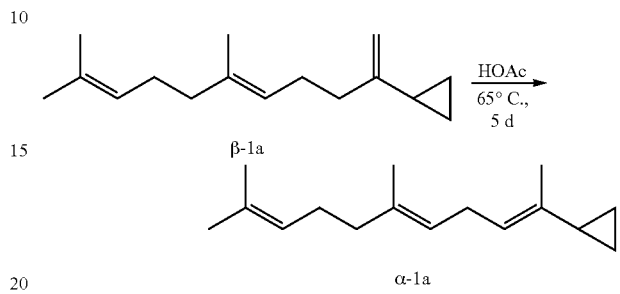

For the synthesis of substrate β-1a see Y. Peng, J.-H. Yang, W.-D. Z. Li, *Tetrahedron* 62, 1209 (2006) and references therein.

A homogeneous mixture of (E)-(6,10-dimethylundeca-1,5,9-trien-2-yl)cyclopropane β-1a (0.5 g, 2.1 mmol), acetic acid (1 g, 17.5 mmol), tetrahydrofurane (2 ml) and water (25 mg) is heated under stirring at 65° C. After 5 days at this temperature GC reveals 11% β-isomer ($t_R$ 8.0 min), 69% α-isomer ($t_R$ 8.2 min) and 13% of acetate 2a ($t_R$ 9.75 (Z) and 9.9 (E) min, E/Z 79:21). The homogeneous mixture is cooled to 25° C. and poured upon water (20 ml) and tert-butyl methyl ether (20 ml). After phase separation the organic phase is washed with conc. aqueous $Na_2CO_3$ (20 ml) and water (20 ml), dried over $MgSO_4$, filtered and evaporated under reduced pressure. The residue is purified by flash chromatography over silicagel with eluent hexane to give pure α-1a as colorless liquid with an α,β-ratio of 92:8 according to GC and an E/Z-ratio of 3:2 according to NMR.

Analytical data of α-1a: $^1$H-NMR ($CDCl_3$, 400 MHz): 5.1-5.2 (s×3H), 2.85 (dd, 1H, 3,4-Z), 2.7 (dd, 1H, 3,4-E), 1.95-2.1 (2×4 H), 1.7 (s, 2×3 H), 1.6 (2 s, 2×6 H), 1.5 (3H, 3,4-E), 1.4 (3H, 3,4-Z), 0.4-0.6 (5H) ppm. $^{13}$C-NMR ($CDCl_3$, 400 MHz) of the E/Z-mixture: 135.4 (s), 134.94 (s), 134.89 (s), 134.5 (s), 131.3 (2 s), 124.6 (d), 124.4 (d), 124.3 (d), 123.3 (d), 123.1 (d), 122.0 (d), 39.69 (t), 39.67 (t), 26.9 (t), 26.72 (t), 26.69 (t), 26.5 (t), 25.6 (2 q), 18.9 (d), 18.7 (q), 17.6 (2 q), 16.03 and 16.01 (2 q), 13.8 (q), 12.3 (d), 4.1 and 3.9 (2 t). ppm. GC/MS (E/Z overlap): 203 (3%, [M-15]$^+$), 175 (8%), 147 (24%), 134 (12%), 133 (14%), 121 (10%), 107 (45%), 105 (11%), 95 (14%), 93 (25%), 91 (20%), 81 (34%), 79 (40%), 69 (100%), 67 (25%), 55 (18%), 53 (24%), 41 (86%), 39 (20%). IR (film): 2967 (s), 2916 (s), 2855 (s), 1443 (s), 1377 (s), 1170 (w), 1105 (m), 1044 (m), 1017 (m), 972 (m), 883 (m), 815 (s), 734 (w).

EXAMPLE 2

Preparation of E,E-Homofarnesylacetate 2a from Δ-Farnesene β-1a

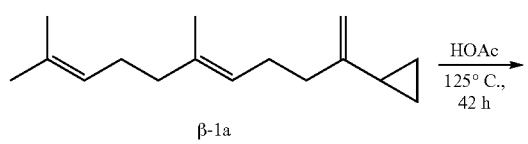

-continued

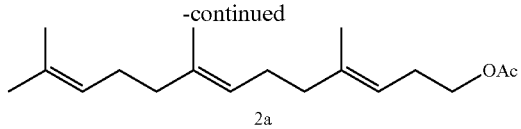

2a

A homogeneous mixture of (E)-(6,10-dimethylundeca-1,5,9-trien-2-yl)cyclopropane β-1a (1 g, 4.6 mmol) and acetic acid (1.4 g, 23 mmol) in a pressure tube is heated under stirring at 125° C. After 5 h GC reveals 5% substrate β-1a, 41% α-isomer and 54% acetate 2a (E/Z 74:26). After 42 h at 125° C., GC reveals complete conversion to 3% α-isomer and 97% of acetate 2a (E/Z 74:26). After cooling to 25° C. the pressure tube is opened and the homogeneous mixture poured upon water (50 ml) and tert-butyl methyl ether (50 ml). The phases are separated and the aqueous phase extracted with tert-butyl methyl ether (25 ml). The combined organic layers are washed with conc. aqueous $Na_2CO_3$ (30 ml) and water (2×50 ml), dried over $MgSO_4$, filtered and evaporated under reduced pressure to give an orange-yellow clear liquid (1 g). Bulb-to-bulb distillation at 130° C./0.1 mbar gives 0.95 g (75%) of homoallyl acetate 2a.

Analytical data of homofarnesol acetate 2a: $^1$H-NMR ($CDCl_3$, 400 MHz): 5.1 (3H), 4.03 (2H), 2.35 (2H), 2.05 (s, 3H), 1.95-2.1 (8H), 1.72, 1.68, 1.63, 1.6 (4 s, 12H) ppm. $^{13}$C-NMR ($CDCl_3$, 400 MHz): 171.1 (2 s, C=O), 138.3 and 138.2 (2 s), 135.4 (Z, s) and 135.1 (E, s), 131.2 (2 s), 124.32, 124.3, 123.9 and 123.8 (2×2 d), 119.8 (Z, d), 119.0 (E, d), 64.3 (Z, t), 64.1 (E, t), 39.7 and 39.6 (2 t), 39.1 (Z, t), 27.5, 27.4, 26.72, 26.66, 26.5, 26.4 (2×3 t), 25.6, 23.4, 21.0, 17.6, 16.1, 16.0, 15.9 (4×2 q) ppm. GC/MS: $r_T$ 9.77 (2,3-Z-isomer), 9.91 (3,4-E-Isomer) min. E/Z=74:26. MS (E-isomer): 278 (1%, M$^+$), 175 (3%), 149 (6%), 136 (28%), 123 (9%), 121 (13%), 107 (16%), 95 (10%), 94 (10%), 93 (20%), 82 (10%), 81 (67%), 79 (13%), 69 (100%), 68 (13%), 67 (20%), 43 (42%), 41 (36%). The MS-data of the Z-isomer are nearly identical. IR (film): 2966 (w), 2915 (w), 2855 (w), 1740 (s), 1442 (w), 1382 (w), 1363 (w), 1230 (s), 1032 (m), 975 (w), 891 (w), 836 (w), 636 (w).

EXAMPLE 3

Preparation of E,E-homofarnesyl acetate 2a from Δ-farnesene α,β-1a

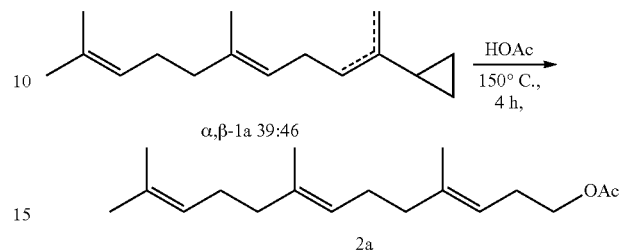

For the preparation of substrate α,β-1a see the patent literature (priority to Givaudan, 2013). Purity: 39% α-isomer, 46% β-isomer, 10% Farnesene.

Acetate 2a was prepared described in example 4 (table 1, run 4) from Δ-farnesene α,β-1a (0.65 g, 3 mmol) in acetic acid (0.9 g, 15 mmol). After 11 h at 150° C., work-up and bulb-to-bulb distillation 0.64 g (89%) of acetate 2a was obtained as clear colorless oil. E/Z-ratio 73:27.

EXAMPLE 4

Rearrangement of (E)-(6,10-dimethylundeca-1,5,9-trien-2-yl)cyclopropane β-1a in different alkanoic acids

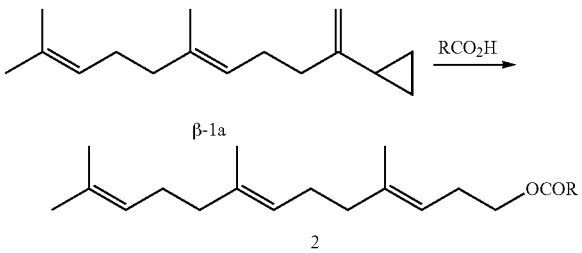

TABLE 1

Rearrangement of Δ-Farnesene β-1a with alkanoic acids.

| run | acid RCO$_2$H | equiv acid | temp [° C.] | time [h] | product R = | % α-1a (GC)$^b$ | %2 (GC) | E/Z |
|---|---|---|---|---|---|---|---|---|
| 1 | HCO$_2$H | 12 | 10° C. | 12 | hH | / | 67% | 72:28 |
| 2 | HCO$_2$H/HOAc | 4/6 | 25° C. | 22 | hH/Me$^a$ | / | 86% | 77:23 |
| 3 | AcOH | 24 | 110° C. | 44 | hMe | 3% | 91% | 74:26 |
| 4 | AcOH | 5 | 150° C. | 11 | hMe | 3% | 93% | 73:27 |
| 5 | EtCO$_2$H | 5 | 150° C. | 20 | hEt | 5% | 91% | 73:27 |
| 6 | tBuCO$_2$H | 8 | 180° C. | 43 | htBu | 9% | 85% | 74:26 |
| 7 | ClCH$_2$CO$_2$H | 5 | 80° C. | 1 | hClCH$_2$ | / | 95% | 73:27 |
| 8 | ClCH$_2$CO$_2$H | 1 | 40° C. | 90 | hClCH$_2$ | / | 100% | 75:25 |
| 9 | Cl$_2$CHCO$_2$H | 1.2 | 25° C. | 73 | hCl$_2$CH | ./. | 96% | 75:25 |
| 10 | Cl$_3$CCO$_2$H | 1.2 | 25° C. | 3 | hCCl$_3$ | ./. | 100% | 75:25 |
| 11 | NC—CH$_2$CO$_2$H | 2 | 65° C. | 5 | hNC—CH$_2$ | | 100% | 73:27 |

Conditions: Δ-Farnesene β-1a mixed with acid RCO$_2$H and heated under stirring in a pressure tube at indicated temperature. Work-up: mixture poured upon water and tert-butyl methyl ether, phases separated, aqueous phase extracted with tert-butyl methyl ether, combined organic layers are washed with conc. aqueous Na$_2$CO$_3$ and water, dried over MgSO$_4$, filtered and evaporated under reduced pressure.
$^a$ratio R = H/Me 56:30
$^b$isolated, crude.

EXAMPLE 5

(7E)-4,8,12-trimethyltrideca-3,7,11-trien-1-yl formate

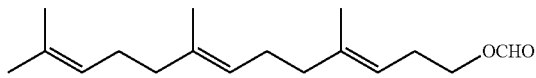

Prepared as described in example 4 table 1, run 1 from (E)-(6,10-dimethylundeca-1,5,9-trien-2-yl)cyclopropane β-1a (0.5 g, 2.1 mmol) and formic acid (1.2 g, 13 mmol). Work-up after 12 h at 10° C. gave (7E)-4,8,12-trimethyltrideca-3,7,11-trien-1-yl formate (0.32 g, 57%) as crude oil.

Analytical data: $^1$H-NMR (CDCl$_3$, 400 MHz): 8.05 (1H, HC=O), 5.1 (3H, HC=), 4.15 (2H, CH$_2$O), 2.4 (2H), 1.95-2.15 (8H), 1.72, 1.68, 1.63, 1.6 (4 s, 12H) ppm. $^{13}$C-NMR (CDCl$_3$, 400 MHz) data are consistent. GC/MS: $r_T$ 9.41 (2,3-Z-isomer), 9.53 (3,4-E-Isomer) min. E/Z=72:28. MS (E-isomer): 264 (1%, M$^+$), 175 (2%), 149 (4%), 137 (8%), 136 (24%), 123 (10%), 121 (11%), 107 (13%), 95 (10%), 94 (10%), 93 (13%), 81 (56%), 79 (11%), 69 (100%), 68 (10%), 67 (16%), 55 (9%), 53 (11%), 41 (43%). The MS-data of the Z-isomer are nearly identical.

EXAMPLE 6

(7E)-4,8,12-trimethyltrideca-3,7,11-trien-1-yl propionate

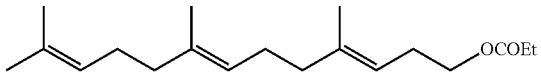

Prepared as described in example 4 (table 1, run 5) from (E)-(6,10-dimethylundeca-1,5,9-trien-2-yl)cyclopropane β-1a (1 g, 4.6 mmol) and propionic acid (1.7 g, 23 mmol). Work-up after 20 h at 150° C. gave (7E)-4,8,12-trimethyltrideca-3,7,11-trien-1-yl propionate (1.2 g, 88%) as crude yellow oil.

Analytical data: $^1$H-NMR (CDCl$_3$, 400 MHz): 5.1 (3H, HC=), 4.05 (2H, CH$_2$O), 2.3 (4H), 1.9-2.1 (8H), 1.72, 1.68, 1.65, 1.6 (4 s, 12H), 1.15 (3H) ppm. $^{13}$C-NMR (CDCl$_3$, 400 MHz) data are consistent. GC/MS: $r_T$ 10.2 (2,3-Z-isomer), 10.3 (3,4-E-Isomer) min. E/Z=73:27. MS (E-isomer): 292 (1%, M$^+$), 203 (1%), 175 (3%), 149 (6%), 137 (8%), 136 (28%), 123 (7%), 121 (13%), 107 (19%), 95 (12%), 94 (12%), 93 (21%), 82 (15%), 81 (74%), 79 (13%), 69 (100%), 68 (12%), 67 (21%), 57 (33%), 41 (33%). The MS-data of the Z-isomer are nearly identical. IR (film): 2967 (m), 2919 (m), 1737 (s), 1450 (m), 1380 (m), 1348 (m), 1273 (w), 1179 (s), 1082 (m), 1015 (m), 836 (w), 807 (w).

EXAMPLE 7

(7E)-4,8,12-trimethyltrideca-3,7,11-trien-1-yl pivalate

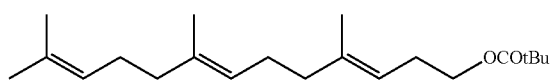

Prepared as described in example 4 (table 1, run 6) from (E)-(6,10-dimethylundeca-1,5,9-trien-2-yl)cyclopropane β-1a (1 g, 4.8 mmol) and pivalic acid (2.3 g, 23 mmol). Work-up after 43 h at 180° C. gave (7E)-4,8,12-trimethyltrideca-3,7,11-trien-1-yl pivalate (1.46 g, 96%) as a yellowish oil.

Analytical data: $^1$H-NMR (CDCl$_3$, 400 MHz): 5.1 (3H, HC=), 4.03 (2H, CH$_2$O), 2.3 (2H), 1.9-2.1 (8H), 1.72, 1.68, 1.65, 1.6 (4 s, 12H), 1.24 and 1.2 (s, 9H) ppm. $^{13}$C-NMR (CDCl$_3$, 400 MHz) data are consistent. GC/MS: $r_T$ 10.45 (2,3-Z-isomer), 10.63 (3,4-E-Isomer) min. E/Z=74:26. MS (E-isomer): 320 (0.5%, M$^+$), 218 (0.5%), 203 (1%), 175 (3%), 149 (8%), 137 (11%), 136 (27%), 123 (8%), 121 (13%), 107 (17%), 95 (12%), 94 (13%), 93 (21%), 82 (15%), 81 (76%), 69 (100%), 68 (12%), 67 (20%), 57 (40%), 41 (38%). The MS-data of the Z-isomer are nearly identical. IR (film): 2967 (m), 2928 (m), 1729 (s), 1480 (m), 1451 m), 1380 (m), 1397 (m), 1377 (m), 1284 (m), 1150 (s), 1036 (w), 975 (w), 939 (w), 838 (w), 770 (w).

EXAMPLE 8

(7E)-4,8,12-trimethyltrideca-3,7,11-trien-1-yl 2-chloroacetate

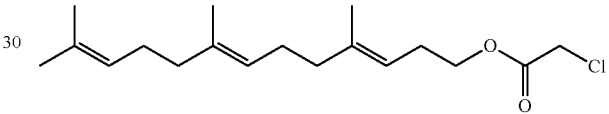

Prepared as described in example 4 (table 1, run 7) from (E)-(6,10-dimethylundeca-1,5,9-trien-2-yl)cyclopropane β-1a (1 g, 4.6 mmol) and 2-chloroacetic acid (2.2 g, 23 mmol). Work-up after 1.5 h at 80° C. gave (7E)-4,8,12-trimethyltrideca-3,7,11-trien-1-yl 2-chloroacetate (1.4 g, 97%) as a yellowish oil.

Analytical data: $^1$H-NMR (CDCl$_3$, 400 MHz): 5.1 (3H, HC=), 4.15 (2H, CH$_2$O), 4.1 (2H, CH$_2$Cl), 2.4 (2H), 1.9-2.1 (8H), 1.72, 1.68, 1.63, 1.6 (4 s, 12H) ppm. $^{13}$C-NMR (CDCl$_3$, 400 MHz) data are consistent. GC/MS: $r_T$ 10.85 (2,3-Z-isomer), 10.99 (3,4-E-Isomer) min. E/Z=73:27. MS (E-isomer): 312 (0.2%, M$^+$), 175 (1%), 149 (4%), 137 (7%), 136 (19%), 123 (10%), 121 (11%), 107 (12%), 95 (10%), 93 (13%), 82 (10%), 81 (60%), 79 (19%), 77 (15%), 69 (100%), 68 (10%), 67 (16%), 53 (10%), 41 (34%). The MS-data of the Z-isomer are nearly identical. IR (film): 2963 (m), 2916 (m), 1737 (s), 1448 (m), 1414 m), 1379 (m), 1308 (m), 1289 (m), 1257 (m), 1167 (s), 989 (m), 929 (w), 836 (w), 788 (w), 697 (w).

EXAMPLE 9

(7E)-4,8,12-trimethyltrideca-3,7,11-trien-1-yl 2,2-dichloroacetate

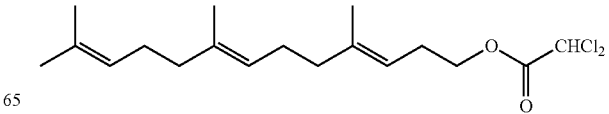

Prepared as described in example 4 (table 1, run 9) from (E)-(6,10-dimethylundeca-1,5,9-trien-2-yl)cyclopropane β-1a (1 g, 4.6 mmol) and 2,2-dichloroacetic acid (0.71 g, 5.5 mmol). Work-up after 6 h at 25° C. gave (7E)-4,8,12-trimethyltrideca-3,7,11-trien-1-yl 2,2-dichloroacetate (1.6 g, quant) as a yellowish oil.

Analytical data: $^1$H-NMR (CDCl$_3$, 400 MHz): 5.9 (1H, CHCl$_2$), 5.1 (3H, HC=), 4.2 (2H, CH$_2$O), 2.4 (2H), 1.9-2.1 (8H), 1.7-1.6 (4 s, 12H) ppm. $^{13}$C-NMR (CDCl$_3$, 400 MHz) data are consistent. GC/MS: r$_T$ 11.18 (2,3-Z-isomer), 11.33 (3,4-E-Isomer) min. E/Z=75:25. MS (E-isomer): 346 (0.5%, M$^+$), 303 (0.5%), 175 (1%), 149 (4%), 137 (14%), 136 (32%), 123 (17%), 121 (18%), 107 (18%), 95 (15%), 93 (19%), 82 (12%), 81 (80%), 79 (15%), 77 (15%), 69 (100%), 68 (13%), 67 (24%), 53 (12%), 41 (42%). The MS-data of the Z-isomer are nearly identical.

EXAMPLE 10

(7E)-4,8,12-trimethyltrideca-3,7,11-trien-1-yl 2,2,2-trichloroacetate

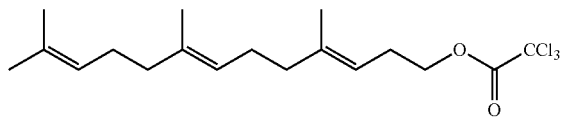

Prepared as described in example 4 (table 1, run 10) from (E)-(6,10-dimethylundeca-1,5,9-trien-2-yl)cyclopropane β-1a (1 g, 4.6 mmol) and 2,2,2-trichloroacetic acid (0.9 g, 5.5 mmol). Work-up after 4 h at 25° C. gave (7E)-4,8,12-trimethyltrideca-3,7,11-trien-1-yl 2,2,2-trichloroacetate (1.6 g, quant) as a yellowish oil.

Analytical data: $^1$H-NMR (CDCl$_3$, 400 MHz): 5.1 (3H, HC=), 4.3 (2H, CH$_2$O), 2.45 (2H), 1.9-2.1 (8H), 1.85-1.55 (4 s, 12H) ppm. $^{13}$C-NMR (CDCl$_3$, 400 MHz) data are consistent. GC/MS: r$_T$ 11.49 (2,3-Z-isomer), 11.66 (3,4-E-Isomer) min. E/Z=75:25. MS (E-isomer): 380 (0.3%, M$^+$), 337 (0.2%), 149 (4%), 137 (10%), 136 (20%), 123 (10%), 121 (11%), 107 (10%), 95 (10%), 93 (10%), 82 (9%), 81 (59%), 69 (100%), 68 (13%), 67 (17%), 41 (31%). The MS-data of the Z-isomer are nearly identical.

EXAMPLE 11

(7E)-4,8,12-trimethyltrideca-3,7,11-trien-1-yl 2-cyanoacetate

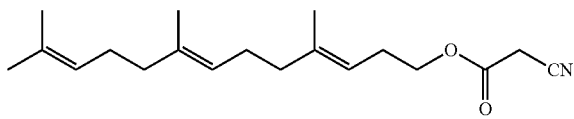 [SMILES: CC(C)=CCC/C(C)=C/CC/C(C)=C/CCOC(=O)CC#N]

Prepared as described in example 4 (table 1, run 11) from (E)-(6,10-dimethylundeca-1,5,9-trien-2-yl)cyclopropane β-1a (1 g, 4.6 mmol) and 2-cyanoacetic acid (0.8 g, 9.2 mmol). Work-up after 5 h at 65° C. gave (7E)-4,8,12-trimethyltrideca-3,7,11-trien-1-yl 2-cyanoacetate (1.37 g, 98%) as a brownish resin.

Analytical data: $^1$H-NMR (CDCl$_3$, 400 MHz): 5.1 (3H, HC=), 4.15 (2H, CH$_2$O), 3.45 (2H), 2.4 (2H), 1.9-2.1 (8H), 1.75-1.6 (4 s, 12H) ppm. $^{13}$C-NMR (CDCl$_3$, 400 MHz) data are consistent. GC/MS: r$_T$ 11.3 (2,3-Z-isomer), 11.43 (3,4-E-Isomer) min. E/Z=73:27. MS (E-isomer): 303 (0.5%, M$^+$), 260 (1%), 149 (4%), 137 (8%), 136 (17%), 123 (14%), 121 (10%), 107 (12%), 95 (10%), 93 (13%), 81 (59%), 79 (10%), 69 (100%), 68 (21%), 67 (18%), 53 (10%), 41 (26%). The MS-data of the Z-isomer are nearly identical.

EXAMPLE 12

(7E)-4,8,12-trimethyltrideca-3,7,11-trien-1-ol

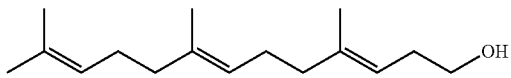 [SMILES: CC(C)=CCC/C(C)=C/CC/C(C)=C/CCO]

A mixture of (E)-(6,10-dimethylundeca-1,5,9-trien-2-yl)cyclopropane β-1a (1 g, 4.6 mmol), dodecane (0.2 g, 1.15 mmol, internal standard) and L-(+)-tartaric acid (1 g, 6.9 mmol) in a pressure tube is heated under stirring at 150° C. After 18 h and complete conversion (according to GC) the mixture is poured on water (50 ml) and toluene (50 ml). The phases are separated and the aqueous phase extracted with toluene (50 ml). The combined organic layers are washed with conc. aqueous Na$_2$CO$_3$ (50 ml) and conc. NaCl (2×50 ml), dried over MgSO$_4$, filtered and evaporated under reduced pressure to give a brownish resin (1.35 g) which is mixed with 30% aqueous KOH (4.3 ml) and stirred at 25° C. for 2 h. GC analysis reveals formation of 96% (7E)-4,8,12-trimethyltrideca-3,7,11-trien-1-ol according to the internal standard. E/Z ratio 68:22. The analytical data of the E-isomer are consistent with the ones from the literature, see for example P. Kocienski, S. Wadman *J. Org. Chem.* 54, 1215 (1989).

EXAMPLE 13

Rearrangement of (E)-(6,10-dimethylundeca-1,5,9-trien-2-yl)cyclopropane β-1a with hydrogen halides

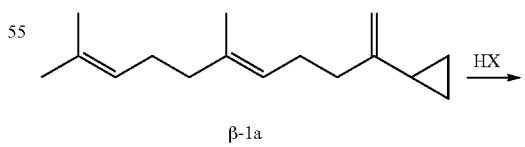

β-1a

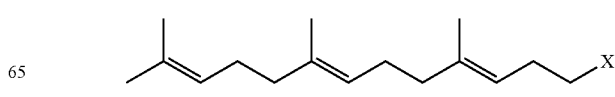

TABLE 2

Rearrangement of Δ-Farnesene β-1a with hydrogen halides. Quantitative conversion.

| run | hydrogen halide | equiv acid | additive, solvent | temp [° C.] | time [h] | product X = | α-1a (GC)[a] | %2 (GC)[a] | E/Z |
|---|---|---|---|---|---|---|---|---|---|
| 1 | HCl 32% | 1 | MeCN | 25° C. | 3 | hCl | / | 100% | 79:21 |
| 2 | HCl 32% | 1.2 | HOAc | 25° C. | 3 | hCl |  | 100% | 77:23 |
| 3 | HCl 32% | 2 | NMP | 100° C. | 2 | hCl |  | 97% | 78:22 |
| 4 | HCl 32% | 1 | 10% SDS[b] | 25° C. | 24 | hCl | 5% | 89% | 82:18 |
| 5 | HBr 48% | 1 | MeCN | 0° C. | 2 | hBr | 2% | 97% | 78:22 |
| 6 | HBr 48% | 1 | HOAc | 25° C. | 1 | hBr |  | 100% | 77:23 |
| 7 | HBr 48% | 1 | 10% SDS[b] | 25° C. | 2 | hBr |  | 100% | 81:19 |
| 8 | HI 67% | 1.1 | MeCN | 0° C. | 2 | hI |  | 100% | 77:23 |

[a] purities fine according to NMR of the crude product.
[b] sodium dodecyl sulfate (SDS).

EXAMPLE 14

(10E)-13-chloro-2,6,10-trimethyltrideca-2,6,10-triene

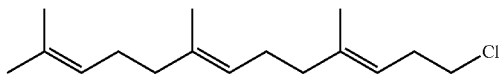 [SMILES: CC(C)=CCC/C(C)=C/CC/C(C)=C/CCCl]

32% aqueous HCl (2.6 g, 23 mmol) is added dropwise to (E)-(6,10-dimethylundeca-1,5,9-trien-2-yl)cyclopropane β-1a (5 g, 23 mmol) in acetonitrile (75 ml) at 0° C. After 1 h at this temperature the homogeneous mixture is stirred for 3 h at 25° C., then poured upon conc. Na$_2$SO$_3$ (50 ml). After the addition of ethyl acetate (100 ml) and phase separation the aqueous phase is extracted with ethyl acetate (50 ml). The combined organic phases are washed with conc. aqueous NaCl, dried over MgSO$_4$, filtered and evaporated under reduced pressure to give 5.75 g (98%) of a crude yellowish oil.

Analytical data: $^1$H-NMR (CDCl$_3$, 400 MHz): 5.1 (3H, HC=), 3.45 (2H, CH$_2$Cl), 2.45 (2H), 1.95-2.15 (8H), 1.75-1.6 (4 s, 12H) ppm. $^{13}$C-NMR (CDCl$_3$, 400 MHz): 138.3 and 138.2 (2 s), 135.5 and 135.3 (2 s), 131.3 and 131.2 (2 s), 124.35 and 124.3 (2 d), 123.9 and 123.7 (2 d) 120.6 and 119.8 (2 d), 44.5 and 44.3 (2 t), 39.7 (2 t), 39.6 (2 t), 32.0, 31.5 and 31.4 (4 t), 26.7 and 26.4 (2 t), 25.6 (2 q), 23.4 (q), 17.6 and 16.2 (2 q), 16.0 and 15.95 (3 q) ppm. GC/MS: r$_T$ 9.17 (2,3-Z-isomer), 9.29 (3,4-E-Isomer) min. E/Z=79:21. MS (E-isomer): 254 (0.5%, M$^+$), 211 (1%), 185 (1%), 136 (14%), 123 (11%), 95 (13%), 81 (51%), 69 (100%), 68 (10%), 67 (17%), 55 (19%), 53 (12%), 41 (41%). The MS-data of the Z-isomer are nearly identical. IR (film): 2964 (m), 2916 (s), 2854 (m), 1719 (w), 1667 (w), 1443 (s), 1377 (m), 1315 (w), 1293 (w), 1239 (w), 1151 (w), 1107 (m), 1047 (w), 983 (w), 888 (w), 832 (m), 718 (m), 657 (m).

EXAMPLE 15

(10E)-13-bromo-2,6,10-trimethyltrideca-2,6,10-triene

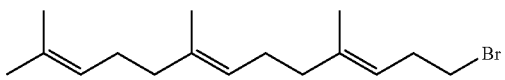 [SMILES: CC(C)=CCC/C(C)=C/CC/C(C)=C/CCBr]

48% aqueous HBr (3.9 g, 28 mmol) is added dropwise to a mixture of (E)-(6,10-dimethylundeca-1,5,9-trien-2-yl)cyclopropane β-1a (5 g, 23 mmol) and sodium dodecyl sulfate (0.25 g, 0.9 mmol) at 0° C. After 30 min at this temperature the homogeneous mixture is stirred for 3 h at 25° C., then poured upon water (50 ml) and tert-butyl methyl ether (100 ml). After phase separation the aqueous phase is extracted with tert-butyl methyl ether (100 ml). The combined organic phases are washed with 10% aqueous Na$_2$CO$_3$ (2×50 ml) and water (2×50 ml) dried over MgSO$_4$, filtered and evaporated under reduced pressure to give 5.89 g (86%) of a crude yellowish oil which is further purified by bulb-to-bulb distillation at 140° C./0.07 mbar to give 4.9 g (72%) of (10E)-13-bromo-2,6,10-trimethyltrideca-2,6,10-triene as yellowish oil. Purity of the main fraction: 89.1% (NMR with standard anisaldehyde).

Analytical data: $^1$H-NMR (CDCl$_3$, 400 MHz): 5.1 (3H, HC=), 3.35 (2H, CH$_2$Br), 2.55 (2H), 1.95-2.15 (8H), 1.55-1.7 (4 s, 12H) ppm. $^{13}$C-NMR (CDCl$_3$, 400 MHz): 138.7 and 138.6 (2 s), 135.5 and 135.2 (2 s), 131.3 (2 s), 124.4 and 124.3 (2 d), 123.9 and 123.7 (2 d), 121.6 and 120.9 (2 d), 39.7 and 39.6 (2 t), 32.9 and 32.8 (2 t), 32.0, 31.7 and 31.6 (4 t), 26.8 and 26.7 (2 t), 26.4 (2 t), 25.7 (2 q), 23.4 (q), 17.7 (q), 16.3 and 16.0 (4 q) ppm. GC/MS: r$_T$ 9.62 (2,3-Z-isomer), 9.75 (3,4-E-Isomer) min. E/Z=81:19. MS (E-isomer): 298 and 300 (0.1%, M$^+$), 255 and 257 (0.2%), 229 and 231 (0.5%), 187 and 188 (2%), 137 (10%), 136 (32%), 123 (15%), 121 (10%), 95 (14%), 93 (10%), 81 (53%), 69 (100%), 68 (10%), 67 (20%), 55 (11%), 53 (10%), 41 (39%). The MS-data of the Z-isomer are nearly identical. IR (film): 2965 (m), 2915 (s), 2854 (m), 1666 (w), 1439 (s), 1377 (s), 1302 (m), 1267 (m), 1204 (m), 1151 (w), 1107 (w), 983 (w), 926 (w), 885 (w), 833 (m), 745 (w), 643 (m).

EXAMPLE 16

Homofarnesol from (10E)-13-bromo-2,6,10-trimethyltrideca-2,6,10-triene

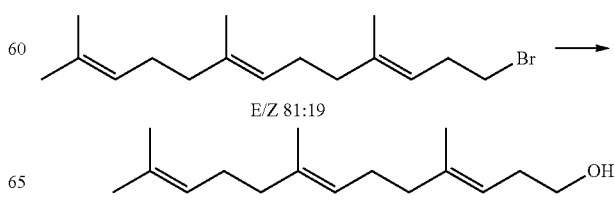

E/Z 81:19

Under conditions described by Moiseenkov et al. (*The New Journal for Organic Synthesis* 22, 225-226, 1990) a mixture of (10E)-13-bromo-2,6,10-trimethyltrideca-2,6,10-triene (1.28 g, 4.3 mmol), KOAc (2.4 g, 24.4 mmol) and 16-crown-6 (80 mg, 0.3 mmol, 7%) is refluxed in acetonitrile (15 ml) is refluxed under stirring and nitrogen for 3 h. At 25° C. water (50 ml) and tert-butyl methyl ether (50 ml) are added, the phases are separated and the water phase extracted with tert-butyl methyl (50 ml). The combined organic phases are washed with conc. aqueous NaCl (50 ml), dried over MgSO$_4$, filtered and evaporated under reduced pressure to give 1.12 g (85%) of the homofarnesyl acetate as crude oil. The analytical data of this intermediate are identical to the ones of the same compound prepared in example 2.

The thus obtained homofarnesyl acetate is added to KOH (0.5 g, 8.5 mmol) in MeOH (4 ml). The red solution is stirred 2 h at 25° C. Work-up as described for the first step (HOAc addition) gives 0.85 g Homofarnesol (84% based on the bromide) as clear yellowish liquid and E/Z 82:18. The analytical data are identical to the ones of the same compound prepared in example 12.

EXAMPLE 17

(10E)-13-iodo-2,6,10-trimethyltrideca-2,6,10-triene

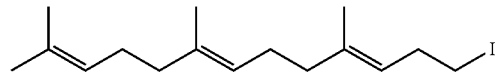 [SMILES: CC(C)=CCC/C(C)=C/CC/C(C)=C/CCI]

67% aqueous HI (0.53 g, 2.75 mmol) is added dropwise to (E)-(6,10-dimethylundeca-1,5,9-trien-2-yl)cyclopropane β-1a (0.5 g, 2.3 mmol) in acetonitrile (10 ml) at 0° C. under stirring. After 2 h at this temperature complete conversion was checked by GC and the orange mixture is poured upon conc. aqueous Na$_2$SO$_3$ (20 ml). After the addition of ethyl acetate (50 ml) and phase separation the aqueous phase is extracted with ethyl acetate (25 ml). The combined organic phases are washed with conc. aqueous NaCl (25 ml), dried over MgSO$_4$, filtered and evaporated under reduced pressure to give 0.72 g (91%) of a crude yellowish oil.

Analytical data: $^1$H-NMR (CDCl$_3$, 400 MHz): 5.1 (3H, HC=), 3.1 (2H, CH$_2$I), 2.55 (2H), 1.95-2.15 (8H), 1.6-1.7 (4 s, 12H) ppm. $^{13}$C-NMR (CDCl$_3$, 400 MHz): 138.2 and 138.1 (2 s), 135.5 and 135.2 (2 s), 131.3 and 131.2 (2 s), 124.4, 124.3, 123.9, 123.72, 121.7 and 123.0 (6 d), 39.7 and 39.6 (2 t), 32.4, 32.3 and 32.1 (4 t), 26.75 and 26.7 (2 t), 26.4 (2 t), 25.7 (2 q), 17.7 (q), 16.3 and 16.0 (3 q), 6.0 and 5.9 (2 t) ppm. GC/MS: r$_T$ 10.14 (2,3-Z-isomer), 10.28 (3,4-E-Isomer) min. E/Z=77:23. MS (E-isomer): 346 (0.2%, M$^+$), 303 (0.4%), 149 (2%), 137 (8%), 136 (28%), 123 (12%), 121 (8%), 95 (18%), 81 (55%), 69 (100%), 67 (30%), 55 (16%), 53 (12%), 41 (43%). The MS-data of the Z-isomer are nearly identical. IR (film): 2964 (m), 2914 (s), 2853 (m), 1741 (w), 1664 (w), 1441 (s), 1376 (m), 1245 (m), 1210 (w), 1164 (s), 1108 (w), 983 (w), 833 (m), 741 (w).

EXAMPLE 18

Preparation of E-Homogeraniol Acetate from Δ-Myrcene

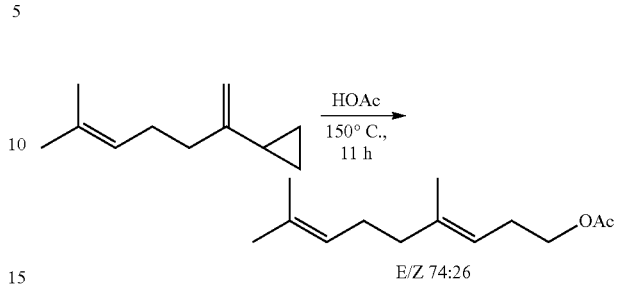

For the preparation of substrate Δ-Myrcene see the patent literature (priority to Givaudan, 2013).

Δ-Myrcene (1 g, 6.7 mmol) and acetic acid (2 g, 33.3 mmol) are heated in a pressure tube 12 h at 150° C. After complete conversion (GC) the homogeneous mixture is poured upon water (100 ml) and tert-butyl methyl ether (50 ml). After phase separation the aqueous phase is extracted with tert-butyl methyl ether (50 ml). The combined organic phases are washed with 10% aqueous Na$_2$CO$_3$ (50 ml) and water (2×50 ml), dried over MgSO$_4$ and evaporated under reduced pressure. The crude product (1.4 g) contains 68% E-homogeraniol acetate, 25% Z-homogeraniol acetate and 4% Δ-Ocimene.

Analytical data of homogeraniol acetate: $^1$H-NMR (CDCl$_3$, 400 MHz): 5.1 (2H), 4.0 (2H), 2.3 (2H), 2.05 (s, 3H), 1.95-2.1 (2H), 1.72, 1.7, 1.61, 1.605, 1.6 (5 s, 9H) ppm. $^{13}$C-NMR (CDCl$_3$, 400 MHz): 171.1 (2 s, C=O), 138.3 and 138.2 (2 s), 131.7 and 131.5 (2 s), 124.1 and 124.0 (2 d), 119.9 (Z, d), 119.0 (E, d), 64.3 (Z, t), 64.1 (E, t), 39.6 (t), 32.0 (t), 27.5 and 27.4 (2 t), 27.0 (q), 25.6 and 25.5 (2 t), 25.7, 23.4, 21.0, 17.7, 17.6 and 17.1 (6 q) ppm. GC/MS: r$_T$ 7.2 (2,3-Z-isomer), 7.34 (3,4-E-Isomer) min. E/Z=74:26. MS (E-isomer): 210 (0.1%, M$^+$), 150 (20%), 135 (12%), 121 (8%), 107 (19%), 82 (18%), 81 (48%), 69 (100%), 67 (21%), 43 (48%), 41 (37%). The MS-data of the Z-isomer are nearly identical. IR (film): 2966 (w), 2916 (w), 1739 (s), 1446 (w), 1364 (m), 1230 (s), 1108 (w), 1032 (m), 975 (w), 894 (w), 836 (w), 635 (w).

EXAMPLE 19

Preparation of E-Homogeraniol Acetate from Δ-Ocimene

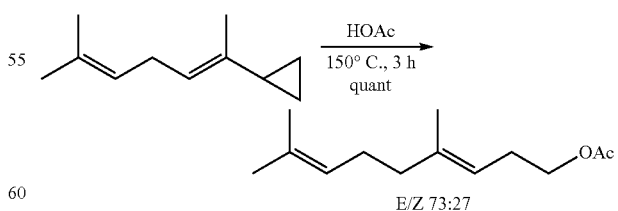

For the preparation of substrate Δ-Ocimene see the patent literature (priority to Givaudan, 2013).

Δ-Ocimene (3 g, 20.2 mmol) and acetic acid (5 g, 0.1 mol) are heated in a pressure tube 3 h at 150° C. Work-up as described in example 17 gives 3.5 g of a dark red liquid which contains 73% E-homogeraniol acetate and 27% Z-homogeraniol acetate according to GCMS. Bulb-to-bulb distillation at 100° C./0.05 mbar gives 2.2 g (52%) homogeraniol acetate as colorless liquid whose analytical data are identical with the ones obtained from homogeraniol acetate as prepared in example 18.

EXAMPLE 20

Preparation of (E)-4,8-dimethylnon-3-ene-1,8-diol from Δ-Myrcenol

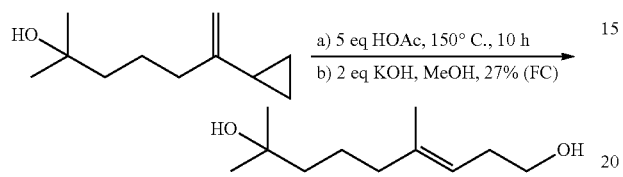

For the preparation of substrate Δ-Hydroxymyrcenol see the patent literature (priority to Givaudan, 2013).

Δ-Hydroxymyrcenol (0.5 g, 3 mmol) and acetic acid (0.9 g, 15 mmol) are heated 10 h at 150° C. Work-up as described in example 17 gives 0.6 g of the crude acetate (E/Z 72:28) with a purity of 75% according to GC. Methanol (6 ml) and 30% aqueous KOH (1.7 ml) are added to the residue. After 1 h stirring at 25° C. conc. aqueous NaCl (50 ml) and tert-butyl methyl ether (50 ml) are added. The phases are separated and the aqueous phase is extracted with tert-butyl methyl ether (50 ml). The organic phases are combined, washed with water (50 ml), dried over MgSO4, filtered and evaporated under reduced pressure to give 0.44 g of the crude diol (E/Z 72:28), which is purified by flash chromatography over silicagel with eluent hexane/tert-butyl methyl ether 1:1 to give (E)-4,8-dimethylnon-3-ene-1,8-diol (0.28 g, 50%) as a colorless oil.

Analytical data: $^1$H-NMR (CDCl$_3$, 400 MHz): 5.1 (1H), 3.65 (2H), 2.3 (2H), 2.1 (2H), 1.45 (4H), 1.23 (s, 6H), 1.21 (s, 1H) ppm. $^{13}$C-NMR (CDCl$_3$, 400 MHz): 138.3 (s), 120.05 (d), 71.0 (s, tBuOH), 62.5 (t), 43.4 (t), 40.1 (t), 31.5 (t), 29.3 (q), 22.6 (2 t), 16.1 (q) ppm. GC/MS: r$_T$ 7.29 (2,3-Z-isomer), 7.38 (3,4-E-Isomer) min. E/Z=94:6. MS (E-isomer): 168 (3%, M$^+$), 153 (4%), 135 (10%), 124 (15%), 112 (37%), 110 (13%), 97 (21%), 82 (18%), 81 (100%), 79 (33%), 69 (38%), 66 (25%), 67 (39%), 59 (53%), 55 (19%), 43 (38%), 41 (29%), 30 (24%). The MS-data of the Z-isomer are nearly identical.

The invention claimed is:

1. A method of forming homoallylic compounds 2 from cyclopropylvinyl precursors 1 in the presence of a Bronsted acid HQ

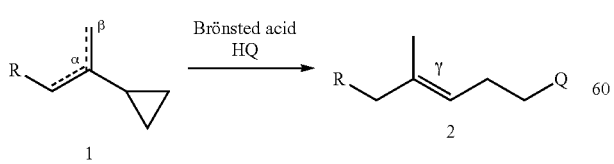

wherein, the Bronsted acid HQ is selected from R'CO$_2$H and/or a hydrogen halide selected from HCl, HBr or HI, wherein R is a C$_{1-30}$ cyclic, polycyclic or acyclic alkyl residue, or an aryl or polyaryl residue, each of which may be saturated or unsaturated, branched or linear, and substituted or unsubstituted; R' is a C$_{1-30}$ alkyl or aryl residue, which may be linear or branched and may be substituted or unsubstituted, and wherein Q is R'CO$_2$ and/or a halide atom.

2. The method of forming a homoallylic alcohol according to claim 1

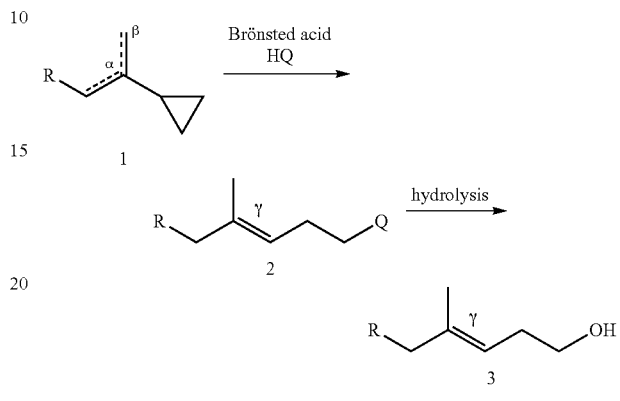

by hydrolysis of rearrangement product 2.

3. The method of forming a homoallylic alcohol according to claim 2, wherein the E/Z ratio is greater than 70:30.

4. The method according to claim 1, wherein the residue R contains carbon-carbon unsaturation.

5. The method according to claim 1, wherein the precursor 1 is a polyprenoid

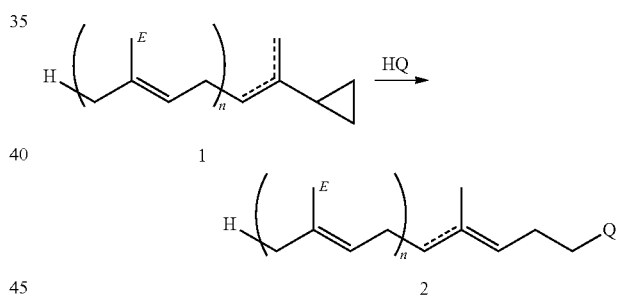

wherein n is 1, 2 or 3.

6. The method according to claim 5 wherein the precursor 1 is a cyclopropanated farnesene.

7. A method of forming the compound:

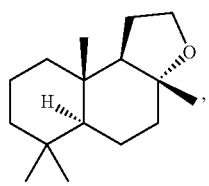

comprising the step of forming E,E-homofarnesol in accordance with the method defined in claim 1, and cyclizing the E,E-homofarnesol so formed using the bacterial enzyme squalene hopene cyclase.

8. The method of forming a homoallylic alcohol according to claim 3, wherein the E/Z ratio is greater than 75:25.

9. The method of forming a homoallylic alcohol according to claim 3, wherein the E/Z ratio is greater than 80:20.

10. The method of forming a homoallylic alcohol according to claim 1

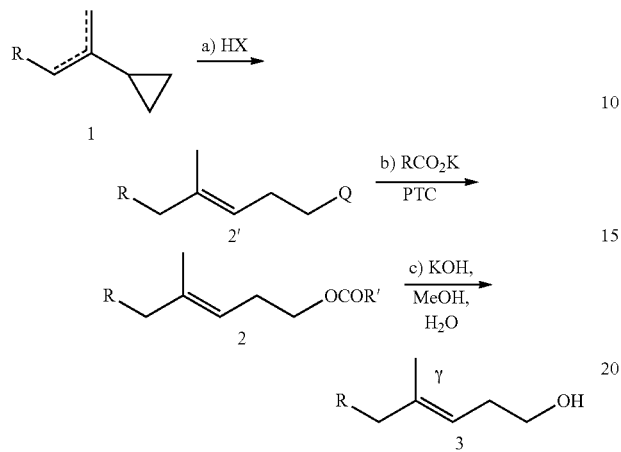

by transesterification and/or nucleophilic substitution of rearrangement product 2' to esters of the general structure 2, said esters being hydrolyzed with aqueous base to homoallylic alcohols of the general structure 3.

\* \* \* \* \*

UNITED STATES PATENT AND TRADEMARK OFFICE
CERTIFICATE OF CORRECTION

PATENT NO. : 9,884,803 B2  
APPLICATION NO. : 15/031132  
DATED : February 6, 2018  
INVENTOR(S) : Schroeder Page 1 of 1

It is certified that error appears in the above-identified patent and that said Letters Patent is hereby corrected as shown below:

In Claim 5, Column 24, Lines 41-45, the presence of a dashed double bond line adjacent the bracketed repeating unit is incorrect. It should read:

" 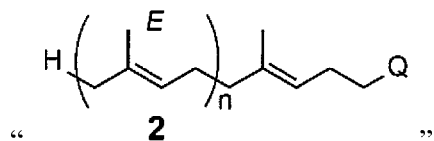 "

In Claim 10, Column 25, Lines 11-15, in the recitation of "Q" as the terminal moiety of the formula 2' intermediate product is incorrect. It should read:

" 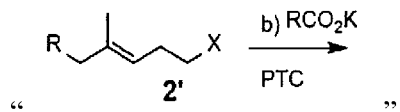 "

Signed and Sealed this  
Eighth Day of May, 2018

Andrei Iancu  
*Director of the United States Patent and Trademark Office*